United States Patent [19]
Whitbourne et al.

[11] Patent Number: 6,110,483
[45] Date of Patent: *Aug. 29, 2000

[54] ADHERENT, FLEXIBLE HYDROGEL AND MEDICATED COATINGS

[75] Inventors: Richard J. Whitbourne, Fairport; Xianping Zhang, Webster, both of N.Y.

[73] Assignee: STS Biopolymers, Inc., Henrietta, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/880,512

[22] Filed: Jun. 23, 1997

[51] Int. Cl.⁷ ....................................................... A61F 2/02
[52] U.S. Cl. .................. 424/423; 424/94.64; 424/78.24; 424/78.27; 514/834; 514/781; 623/1; 623/3; 604/187; 604/313; 604/319; 427/2.3; 427/569; 427/421; 427/429; 427/430.1
[58] Field of Search ................................ 424/423, 94.64, 424/78.24, 78.27; 514/834, 781; 623/1, 3, 900; 604/187, 313, 319; 427/2.3, 569, 421, 429, 430.1

[56] References Cited

U.S. PATENT DOCUMENTS

| | | | |
|---|---|---|---|
| 3,695,921 | 10/1972 | Shepherd et al. | 117/72 |
| 3,939,049 | 2/1976 | Ratner et al. | 204/159.13 |
| 4,055,682 | 10/1977 | Merrill | 427/2 |
| 4,100,309 | 7/1978 | Micklus et al. | 427/2 |
| 4,373,009 | 2/1983 | Winn | 428/424.2 |
| 4,459,317 | 7/1984 | Lambert | 427/2 |
| 4,459,318 | 7/1984 | Hyans et al. | 427/36 |
| 4,589,873 | 5/1986 | Schwartz et al. | 604/265 |
| 4,642,267 | 2/1987 | Creasy et al. | 428/413 |
| 4,769,013 | 9/1988 | Lorenz et al. | 604/265 |
| 4,773,901 | 9/1988 | Norton | 604/265 |
| 4,781,703 | 11/1988 | Walker et al. | 604/264 |
| 4,835,003 | 5/1989 | Becker et al. | 427/2 |
| 4,847,324 | 7/1989 | Creasy | 525/57 |
| 4,867,174 | 9/1989 | Skribiski | 128/772 |
| 4,876,126 | 10/1989 | Takemura et al. | 428/35.7 |
| 4,883,699 | 11/1989 | Aniuk et al. | 428/36.9 |
| 4,884,579 | 12/1989 | Engelson | 128/772 |
| 4,906,237 | 3/1990 | Johansson et al. | 604/265 |
| 4,950,257 | 8/1990 | Hibbs et al. | 604/265 |
| 5,001,009 | 3/1991 | Whitbourne | 428/412 |
| 5,041,100 | 8/1991 | Rowland et al. | 604/265 |
| 5,084,315 | 1/1992 | Karimi et al. | 428/36.6 |
| 5,331,027 | 7/1994 | Whitbourne | 524/37 |
| 5,416,131 | 5/1995 | Wolff et al. | 523/105 |
| 5,443,907 | 8/1995 | Slaikeu et al. | 428/375 |
| 5,525,348 | 6/1996 | Whitbourne et al. | 424/423 |
| 5,620,738 | 4/1997 | Fan et al. | 427/2.3 |
| 5,824,048 | 10/1998 | Tuch . | |
| 5,853,745 | 12/1998 | Darouiche . | |

FOREIGN PATENT DOCUMENTS

| | | |
|---|---|---|
| 0 184 465 | 6/1986 | European Pat. Off. . |
| 0 328 421 | 8/1989 | European Pat. Off. . |
| 0 407 965 | 1/1991 | European Pat. Off. . |
| 2064556 | 6/1991 | United Kingdom . |

OTHER PUBLICATIONS

Kirk–Othmer, "Concise Encyclopedia of Chemical Technology," John Wiley & Sons, 1985, pp. 24–26, 90–92, 431–433, 437–439, 814–818, 867–868, 1115–1117, and 1225–1228.

Jacqueline I. Kroschwitz, "Concise Encyclopedia of Polymer Science and Engineering," John Wiley & Sons, 1990, pp. 15–20, 47–48, 344–349, 350–351, 716–719, 1119, 1140–1141, 1230–1232, and 1264–1272.

Malcolm P. Stevens, "Polymer Chemistry: An Introduction," Second Edition, Oxford University Press, 1990.

"Acryloid Acrylic Resins for Industrial Finishing," Rohm and Haas, Sep. 1985.

"RHOPLEX® B–15J Heat–Sealable, Acrylic Binder for Nonwovens" Rohm and Haas Company, 1995.

"CYMEL® 303 Crosslinking Agent" CYTEC Industries Inc., 1995.

"EPOTUF® 37–618 Polyamide Solution", Product Bulletin, Reichhold Chemicals, Inc., Mar. 1993.

EPOTUF® Epoxy Resin Solution 38–505, Product Bulletin, Reichhold Chemicals, Inc., Nov. 1987.

International Search Report dated Feb. 2, 1999.

*Primary Examiner*—Michael A. Williamson
*Attorney, Agent, or Firm*—Michael A. Gollin; Venable

[57] ABSTRACT

The adherent coating of the invention comprises a stabilizing polymer together with an active agent (a hydrophilic polymer and/or a bioactive agent) in a layer bonded to the surface of a medical device. This invention encompasses the coating liquids used for coating medical devices, methods of coating the devices, and the coated devices. The stabilizing polymer is selected to entrap the active agent in a coating that has a high degree of flexibility and has improved bonding to a wide variety of substrates. Preferred stabilizing polymers are cross-linkable acrylic and methacrylic polymers, ethylene acrylic acid copolymers, styrene acrylic copolymers, vinyl acetate polymers and copolymers, vinyl acetal polymers and copolymers, epoxy, melamine, other amino resins, phenolic polymers, copolymers thereof, and combinations.

40 Claims, No Drawings

ADHERENT, FLEXIBLE HYDROGEL AND MEDICATED COATINGS

BACKGROUND OF THE INVENTION

This invention relates to coatings for biomedical devices in which an active agent is entrapped in a stabilizing polymer that provides improved bonding and flexibility. The active agent may be a hydrophilic polymer that produces a lubricious hydrogel, a bioactive agent that confers a physiological effectiveness, or a combination, so that the coating may be a hydrogel and/or a medicated coating.

Known lubricious coatings that may be applied to biomedical devices include coatings of polyvinylpyrrolidone (PVP), polyurethane, acrylic polyester, vinyl resin, fluorocarbons, silicone, rubber, and some combinations. Whitbourne, U.S. Pat. No. 5,001,009, relates to a hydrophilic coating containing PVP and cellulose ester polymers. Whitbourne, U.S. Pat. No. 5,525,348 discusses medicated polymer coatings based on cellulose esters.

Known hydrogel and medicated coatings for insertable devices have disadvantages, including poor adherence to inert polyolefin and metal surfaces, too much friction, too little permanence, and difficult or hazardous methods of application. With polyurethane-PVP coatings, little control can be exerted over the degree of lubricity and resistance to wet abrasion of the coatings, and such coatings are often unstable. PVP-cellulose ester coatings may be brittle, and are difficult to bond to certain substrates. Hydrogels can absorb several times their weight in water when placed in an aqueous environment, resulting in water penetrating to the coating/substrate interface, which makes adhesion failure a serious problem.

In order to solve these problems an improved polymer blend is needed for a coating for a medical device which may be formed as a hydrogel and/or a medicated coating, bonds well when dry, resists wet abrasion, is flexible enough to remain coherent on flexible devices, provides improved adherence to a wide variety of substrates, and can be prepared from chemically stable and biocompatible solvents.

SUMMARY OF THE INVENTION

The adherent coatings of the invention comprise a stabilizing polymer in which an active agent is entrapped, the active agent being a hydrophilic polymer and/or a bioactive agent, and the coating being flexible and bonded to the surface of a medical device. This invention encompasses the coating liquids used for coating medical devices, methods of coating the devices, and the coated devices. The coating layer may be formed of a single coating application or successive applications of the coating components.

The invention satisfies a long felt need for more flexible, adherent hydrogel and medicated coatings for insertable medical devices. The invention succeeds where previous efforts at providing such coatings have failed, despite extensive efforts in a crowded and mature art. The invention eliminates the need for cellulose esters, polyurethane, and other coating polymers employed in the prior art, with good resistance to wet abrasion, and enhanced flexibility and adhesion. The materials and methods of the invention were not previously known or suggested, and their advantages were not previously appreciated.

The invention encompasses a coating applied to a surface of a medical device, the coating comprising: (a) a stabilizing polymer selected from the group consisting of cross-linkable acrylic and methacrylic polymers, ethylene acrylic acid copolymers, styrene acrylic copolymers, vinyl acetate polymers and copolymers, vinyl acetal polymers and copolymers, epoxy, melamine, other amino resins, phenolic polymers, copolymers thereof, and combinations; and (b) an active agent selected from the group consisting of a hydrophilic polymer selected to interact with the stabilizing polymer so as to produce a lubricious hydrogel, and a bioactive agent, and a combination; the active agent being entrapped in the stabilizing polymer such that the coating adheres to the surface when dry and wet, and remains coherent despite flexing of the surface.

Preferably, the stabilizing polymer is cross-linkable and the coating comprises a cross-linker for the stabilizing polymer, such as epoxy resin, melamine resin, other amino resin, and phenolic resin. The stabilizing polymer may be selected from a carboxyl function acrylic polymer, hydroxyl function acrylic polymer, amine function acrylic polymer, methylol function, and amide function acrylic polymer. It may be a cross-linkable acrylic selected from methylmethacrylate, butylmethacrylate, isobutylmethacrylate, ethylmethacrylate, methylacrylate, ethylacrylate, acrylic acid, methacrylic acid, styrene methacrylate, and styrene acrylate, and copolymers thereof.

The surface of the medical device preferably comprises a material selected from the group consisting of stainless steel, nickel, gold, chrome, nickel titanium alloy, platinum, another metal, silicone, polyethylene, other polyolefins, polyesters, other plastics, glass, polyurethane, acetal, polyamide, and polyvinyl chloride.

The medical device may be chosen from any insertable or partially insertable device for invasive or similar procedures, such as needles, guide wires, catheters, surgical instruments, equipment for endoscopy, wires, stents, angioplasty balloons, wound drains, wound dressings, arteriovenous shunts, gastroenteric tubes, urethral inserts, laparoscopic equipment, pellets, and implants.

The bioactive agent is preferably selected from the group consisting of a pharmaceutical agent, a salt, an osmotic agent, and DNA. The coating may comprise a surfactant, a colorant, or plasticizer(s).

The stabilizing polymer may be concentrated in an inner layer and the active agent in an outer layer. In preferred embodiments, the coating thickness is less than about 50 microns, the active agent is a hydrophilic polymer and the coating is a hydrogel, optionally with a biotctive agent.

The coating resists wet abrasion and remains coherent without cracks despite flexing when applied to difficult to coat inert surfaces such as stainless steel. The selection of stabilizing polymer may be independent of whether the stabilizing polymer is present in the substrate.

A method according to the invention applies a coating to a medical device having an inert surface by applying to the surface a coating liquid comprising a stabilizing polymer and a coating liquid comprising an active agent and drying to remove liquids such that the active agent is entrapped in the stabilizing polymer and the coating adheres to the surface when dry and wet, and remains coherent despite flexing of the surface. A single or multiple coating liquids may contain the stabilizing polymer and the active agent or agents. The liquids may be applied by dipping, spraying, brushing, or wiping, or other methods known in the art. The device surface may be pretreated by gas plasma or other ionizing treatment before the applying step, and/or a precoat layer may be applied. The drying typically comprises heating the coating to at least about 50° C.

When the medical device surface includes one of the stabilizing polymers of the invention, the coating may be prepared by applying a coating liquid comprising a solvent capable of attacking the device surface, and an active agent such that the active agent is entrapped in the surface polymer and the coating adheres to the surface when dry and wet, and remains coherent despite flexing of the medical device.

A kit according to the invention comprises a liquid comprising the stabilizing polymer and a liquid comprising the active agent, the liquids being the same or separate, and the stabilizing polymer and the active agent being selected to produce on the medical device a coherent flexible coating that has wet and dry adhesion. If the liquids are separate, the liquid comprising the active agent preferably comprises a cross-linker for the stabilizing polymer. The liquid or liquids may be based on a solvent selected from the group consisting of water, xylene, tetrahydrofuran, cyclohexanone, ethanol, butyrolactone, butanol, trichloroacetic acid, benzyl alcohol, isobutyl acetate, methyl ethyl ketone, Aromatic 150, toluene, and butyl cellosolve. The stabilizing polymer liquid may be an aqueous cross-linkable acrylic dispersion.

The stabilizing polymer is preferably a water-insoluble polymer that does not significantly react with the hydrophilic polymer or bioactive agent in solution, has low water absorption, provides a high degree of flexibility, and has improved bonding to a wide variety of substrates. Suitable commercial products that may be used in the invention include acrylics such as ACRYLOID® (Rohm & Haas) AT-63, AT-51, AT-81, WR-97; ethylene acrylic acid copolymers such as PRIMACOR™ (DOW) 5989, 5990; melamine resins such as CYMELO® hexamethoxymethylmelamine (CYTEC Industries) 303, 370, 380; epoxies such as EPON (Shell) 1001; and polyvinylbutyral such as BUTVAR B-79 (Monsanto). The preferred acrylic stabilizing polymers include reactive groups such as hydroxyl or carboxyl that can react with epoxies but do not render the polymer hydrophilic.

In one embodiment, the inventive coating includes a hydrophilic polymer such as a water soluble polyolefin such as a hydrophilic vinyl polymer having polar pendant groups, a polyacrylate or methacrylate having hydrophilic esterifying groups, a polyether, a polyethylene glycol, or other polymer with hydrophilic characteristics as known in the art. The hydrophilic polymer is preferably PVP or PVP/vinyl acetate such as PVP/VA (GAF) E-335 and E-635. The stabilizing polymer need not react with the hydrophilic polymer, although in some embodiments of the invention stabilizing polymers are used which can crosslink with themselves thus forming a crosslinked network and entrapping hydrophilic polymer molecules in the crosslinked network. In another embodiment, the coating comprises a bioactive agent in addition to the stabilizing polymer, either instead of or in addition to the hydrophilic polymer. The bioactive agent may be an antithrombogenic, antibacterial, anticancer, gene therapy, or other agent, present in an amount that is effective to achieve the desired effect under the conditions to which the coating is subjected. This generally includes a time release effect attributable to the interaction of the bioactive agents with the stabilizing polymer.

Further objectives and advantages that can be attained by the present invention will become apparent from the detailed description.

DETAILED DESCRIPTION OF THE INVENTION

In describing preferred embodiments of the present invention illustrated in the examples, specific terminology is employed for the sake of clarity. However, the invention is not intended to be limited to the specific terminology so selected, and it is to be understood that each specific element includes all technical equivalents which operate in a similar manner to accomplish a similar purpose.

The chemical structure and physical characteristics of hydrogels and medicated coatings for medical devices are poorly understood and difficult to predict. Research in this field depends heavily on empirical results as to the performance of particular coating compositions under relevant conditions. Thus, the special advantages of the inventive coatings could not have been appreciated from the prior art.

The coatings of the invention are blends, defined as a mixture so combined as to render the components indistinguishable from each other. Such a coating is a complex structure that may have one or a combination of several physical forms. It is a coating, defined as a material that forms a thin continuous layer over the substrate, and could be referred to as a film. It may be a solid mixture of the stabilizing polymer and hydrophilic polymer or bioactive agent, additives, and possibly solvent residues blended together. Alternatively, the coating may be a complete solid solution, that is a mixture uniformly dispersed throughout the solid phase with homogeneity at the molecular or ionic level, or it may be a combination of dissolved and mixed components, such as a mixture of a polymer coating solution and insoluble particles in suspension. The coating may take the form of a composite, that is a structure composed of a mixture or combination of polymer and other constituents that differ in form and chemical composition and are essentially insoluble in each other. It may be referred to as a matrix of polymer in which other components are entrapped. The coating may comprise separate layers, discrete or intermingled, each of which may have any or several of these forms.

Thus, the structure of the coating is intermingled molecules of the polymer components and other coating components, in a homogeneous distribution with attributes of a solid phase mixture and solution. During drying, the polymers presumably become tangled together and obtain the desired characteristics of a hydrogel or stable matrix capable of sustained release of a bioactive agent. This relationship between the components is referred to as an entrapment of the active agent in the stabilizing polymer, with the result that the active agent is not solubilized or removed directly from the coating, as it would be without the stabilizing polymer, and the coating adheres to the substrate well enough to withstand dry handling and wet conditions expected in use.

The stabilizing polymer according to the invention is non-toxic and physiologically acceptable. Most of the suitable stabilizing polymers dissolve in organic solvents, and they have a poor affinity for water, produce a water-insoluble coating film when applied to a substrate with the other coating components, and adhere to the substrate or a pre-coated substrate under applications involving insertion into tissue and removal. Such a polymer will generally absorb less than about 30%, preferably less than about 10% of its weight in water. The amount and kind of stabilizing polymer must also be adapted to maintain coating integrity during swelling of the coating due to hydration of the hydrophilic polymer. Thus, the stabilizing polymer stabilizes hydrophilic polymers and bioactive agents and renders them entrapped on the coated surface.

The hydrophilic component is non-toxic and physiologically acceptable. It dissolves in organic solvents, and is partially or totally soluble in water. It absorbs and retains water and swells when wet in conjunction with the other coating components, absorbing at least its own weight in water, preferably more than about five times its weight, most preferably more than about ten times its weight, to produce a hydrogel that is suitably lubricious when wet. The amount and kind of hydrophilic polymer may readilyhydrophocted in conjunction with the hydrophobic polymer and hydrating agent to satisfy these criteria. Such hydrophilic polymers are well-known in the art, and a person of ordinary skill can readily find appropriate hydrophilic polymers that are compatible with the stabilizing polymer in the sense that together they form a hydrogel.

The hydrophilic component may be of any of the classes discussed in *Concise Encyclopedia of Polymer Science and Engineering,* Kroschwitz, ed. (Wiley 1990), pp. 458–59, which is incorporated herein by reference. Polymers such as polyvinylpyrrolidone, polyethylene glycol, polyethylene oxide, or polyvinyl alcohol are acceptable, alone or in combination. Examples of suitable hydrophilic polymers include homopolymers or copolymers of the following compounds: polyolefins such as vinyl polymers having polar pendant groups, N-vinylpyrrolidone, N-vinyllactam, N-vinyl butyrolactam, N-vinyl caprolactam, sodium styrene sulfonate monomer, 2-acrylamido-2-methylpropane sulfonic acid, sodium vinyl sulfonate, vinyl pyridine, acrylates or methacrylates having hydrophilic esterifying groups. Other hydrophilic polymers include polyethers, polyethylene glycol, polysaccharides, hydrophilic polyurethanes, polyhydroxyacrylates, polymethacrylates, and copolymers of vinyl compounds and hydroxyacrylates or acrylic acid, so long as the appropriate hydrophilicity is present. Other examples include dextran, xanthan, hydroxypropyl cellulose, methyl cellulose, polyacrylamide, and polypeptides. Other hydrophilic components are known to persons of skill in the art. The concentration and type of this component in the coating is sufficient to absorb water and become lubricious when wet, while being compatible with the stabilizing polymer component and (if present) the bioactive agent.

The concentration of hydrophilic polymer in the coating is preferably between about 10% and about 98%, most preferably between about 70% and about 90% of the coating or outer sublayer in which it is present. In a multi-layer coating, where the hydrophilic component is present as a top coat, the top coat may also optionally include up to about 10% or more of a hydrophobic polymer. Some stabilizing polymers are less hydrophilic, and contribute some of the stabilizing characteristics defined above for a hydrophobic polymer, and some hydrophobic polymers have higher absorbency of water, so that greater or lesser amounts of the particular components may be desirable to achieve the objects of the invention.

Substrates to which coatings according to the invention may be applied include polyurethane, polyvinylchloride, acetal, polyethylene, polypropylene, polyamide, polyester, silicone, and metals such as stainless steel, platinum, gold, nickel, titanium, nickel-titanium alloys, chrome, and others. The advantages of the inventive coating are particularly evident on stainless steel wires, polyethylene catheters, and other notoriously difficult to coat substrates. Preferred devices include needles, guide wires, catheters, surgical instruments, equipment for endoscopy, wires, stents, angioplasty balloons, wound drains, arteriovenous shunts, gastroenteric tubes, urethral inserts, laparoscopic equipment, pellets, or implants.

Preferred stabilizing polymers are based on the following classes, as defined herein and as would be understood by one of ordinary skill based on e.g. *Concise Encyclopedia of Polymer Science and Engineering,* Kroschwitz, ed. (Wiley 1990), or *Kirk-Othmer Concise Encyclopedia of Chemical Technology,* (Wiley 1985), Acrylics, e.g. polymers and copolymers of acrylic acid and methacrylic acid and esters thereof, as defined for example in ACRYLOID Thermoplastic Acrylic Ester Resins for Industrial Finishing, Rohm & Haas, Bulletin 82A37 (1987), in particular cross-linkable acrylics with at least one component containing carboxyl, hydroxyl, amide, or methylol groups. The following ACRYLOID polymers with functional groups given are preferred: AT-51 (hydroxyl), AT-63 (hydroxyl), AT-81 (carboxyl), and WR-97 (hydroxyl). Cross-linkable acrylic emulsions such as RHOPLEX B-15J (Rohm & Haas), and styrene acrylic emulsions such as AROLON® 820-W-49 (Reichhold) may also be used.

Amino resins, particularly melamine, and derivatives such as methylated or butylated, including hexamethoxymethylmelamine (HMMM).

Phenolic resins.

Epoxy resins, particularly cured epoxy polymers such as EPOTUF® 38-505 (Reichhold), and preferably those cured with polyamide, such as EPOTUF® 37-618 (Reichhold).

Vinyl polymers, particularly vinyl acetate, vinyl acetals such as polyvinyl butyral, and ethylene vinyl acetate copolymers.

Other appropriate polymers having the requisite characteristics will be apparent to persons of ordinary skill. The polymers preferably, but not necessarily, contain reactive groups or points of reactivity such as hydroxyls, mono-, di- and tertiary amines, acids such as carboxyl, amides, or other groups which represent points of chemical reactivity. In the case of the acrylics, this is referred to as having a "functionality" that is cross-linkable. The polymers and points of chemical reactivity are able to form attractive forces such as hydrogen bonding toward the medical device surface, and also toward the hydrophilic polymer and/or bioactive agent. Such bonds are very strong, and provide desirable adhesion and flexibility to the coating presumably without requiring covalent, ionic, or other links.

Polymers with reactive groups are preferred with substrates like metals. However, polymers lacking such groups such as acrylic or styrene copolymers may also be used effectively.

The reactive groups can also react to form a cross-linked matrix or help to form a cross-linked matrix. If desired, cross-linkers such as urea resins, melamines, isocyanates, phenolics, and others may be incorporated to interact with the points of chemical reactivity on the polymer chains to cross-link the polymers of the invention with themselves. Alternatively, cross-linkers may react with themselves as stabilizing polymers to form a cross-linked matrix in which the hydrophilic polymer is enmeshed, resulting in an adherent, flexible coating. Cross-linking is useful in promoting effective adhesion by ensuring that the solvents do not attack and degrade the polymer layer excessively when subsequent layers are applied.

Coatings according to the invention may be prepared with polymers that lack points of reactivity, such as acrylic or styrene polymers or copolymers. Likewise, coatings may be made without cross-linking. However, with such coatings a greater coating thickness may be required or desirable than with layers made of polymers with points of reactivity and layers with cross-linking, in order to achieve a high degree of adhesion and flexibility according to the invention. For example, cross-linked coatings with polymers having reactive groups may be about two to about ten microns thick, in contrast with a coating of an acrylic styrene copolymer, with a hydrogel layer on top, and a total thickness of about 30–40 microns.

The coatings of the present invention are extremely durable, even when subjected to adhesion and flexing tests, as shown in the examples. Such enhanced adhesion and flexibility is a surprising result. The coatings according to the invention may be applied to the surface of a biomedical device or other device with sufficient thickness and permanence to retain the coating's desirable qualities throughout the useful life of the coated device. The coatings of the invention are nonreactive with living tissue and are non-thrombogenic in blood.

The coatings of the invention may be thin, on the order of 2 to 100 microns, preferably less than about 50 microns, and coherent in that they form a continuous surface layer. They are resistant to removal on prolonged soaking in aqueous fluids, and are adherent to a wide variety of substrates.

The coatings may be applied by various techniques such as dip, pour, pump, spray, brush, wipe, or other methods know to those skilled in the art. The coating solutions have low viscosities, typically less than 100 CPS, and have good spreading properties. The coatings are preferably baked at elevated temperatures, typically 50° C. to 100° C., to drive off the organic solvents. It may be necessary to treat some surfaces like polyethylene with gas plasma or other ionizing treatment to promote interaction with the coating and adhesion to the substrates.

The coating may contain polymers in addition to the stabilizing polymer such as polyurethane, polyester, styrene polybutadiene, polyvinylidene chloride, polycarbonate, and polyvinyl chloride, preferably in the inner layer to promote adhesion to the surface of the device. The disclosure of U.S. Ser. No. 08/791,440, "Bonding Layers for Medical Device Surface Coatings" is hereby incorporated by reference in its entirety for further enabling details. Such additional polymers are not necessary to achieving the advantages of the invention, in contrast to prior art coatings relying on some of these polymers.

The method of preparing the coatings of the invention employs stable, non-toxic solutions which may be stored and handled with minimal precautions. The method of applying the coating of the invention may comprise preparing a first organic solution of from about 0.01% to about 30% (w/w) of stabilizing polymer, preferably from about 0.2% to about 10%, applying the solution to a substrate surface, and evaporating the solvent, preferably at elevated temperature, then preparing a second solution of from about 0.001% to about 30% (w/w) active agent, preferably from about 0.5% to about 20%, applying it to the treated surface substrate and evaporating the solvents at room or elevated temperature.

The stabilizing polymer solution may also contain from about 0.01% to about 20% of active agent, preferably from about 0.1% to about 5%. The active agent solution may also contain from about 0.01% to about 30% of stabilizing polymer, preferably from about 0.1% to about 10%. Alternatively, the stabilizing polymer and active agent can be prepared in a single solution and applied in a single step.

A plasticizing agent may be included with the stabilizing polymers, in a concentration of from about 0.01% to about 20%, preferably from about 0.1% to about 10% (w/w). The plasticizing agent may be camphor, castor oil, dioctyl phthalate, acetyl tributyl citrate, dibutyl sebacate, sebacic acid, alkyl resin, polyethylene-glycol, polypropylene-glycol, dibutylphthalate, or other commonly known plasticizers, singly or in combination. The plasticizing agent may be incorporated into the solution of hydrophilic polymer or stabilizing polymer as needed to enhance flexibility of the coating which may be preferable when the object to be coated is likely to bend during use. However, suitable flexibility is achievable according to the invention with coating compositions that lack such additional plasticizers.

Solvents for the stabilizing and adherent polymer include organic solvents such as ketones, esters, toluene, lactones, dimethylformamide, halogenated solvents, tetrahydrofuran, dioxane, amines, glycol butyl ether, alkyl acetates, acetonitrile, and other commonly known organic solvents. The less toxic solvents are preferred. The inclusion of small amounts of hydroxyl groups such as alcohols and moisture in the solvent does not have a significant detrimental effect on the coating and method of the invention. Solvents for the hydrophilic polymer include most of the above as well as alcohols, acetic acid, and like solvents. A solvent system may be selected that is capable of dissolving all the constituents of the coating in a uniform solution, can act as a co-solvent in the coating layer and is non-toxic. If desirable, a solvent may be selected that interacts with the particular substrate surface to promote adhesion.

In one embodiment of the present invention, the article to which the coating is to be applied has a polymer surface comprising the stabilizing polymer, and an "active" solvent is used which obviates the need for the inner layer or base coat by permitting a lubricious hydrophilic layer (or top coat) to be applied directly onto the polymer surface of the article. In this embodiment, the term "active solvent" is defined as a cosolvent for both the polymer or polymer mixture comprising the polymer surface or at least one or more of the polymers in cases of mixed polymer substrates and for the coating polymer(s).

The hydrophilic medicated coatings of this invention are highly lubricious when wetted with an aqueous solution such as body fluid, or a lower alcohol such as ethanol or methanol, yet they are substantially less slippery when dry. Thus, an implant coated according to the invention remains non-slippery for ease of handling and preparation, but becomes lubricious when implanted, so as to protect the patient. The lubricity of the coating can be adjusted within a desirable range from ultra lubricious to not lubricious by adjusting the ratio of the hydrophilic to stabilizing polymers.

A coating according to the invention may be applied to the surface of a biomedical or other device with sufficient thickness and permanence to retain the coating's desirable qualities throughout the useful life of the coated device. The coatings of the invention are non-reactive with living tissue and are non-thrombogenic in blood.

The coatings of the invention have beneficial characteristics for use on the surfaces of devices such as biomedical implants. The coating may be hydrophilic, absorbing water and swelling in an aqueous environment to become a hydrogel, so that the coating has lubricant properties, and is significantly more slippery when wet than when dry.

Various physiologically active agents may be incorporated into the hydrogel coating. Such agents maybe incorporated in order to ameliorate certain problems which typically occur on the surfaces of implanted medical devices. For instance, antithrombogenics such as heparin-quaternary ammonium complexes may be incorporated into the hydrogel systems. Antimicrobial agents such as various silver compounds, quaternary ammonium compounds such as benzalkonium chloride, phenol derivatives such as thymol, and antibiotics such as gentamycin, norfloxacin, and rifamycin can be incorporated into the hydrogel system. The hydrogel coatings can also be used as reservoirs for targeted drug delivery. Materials such as DNA or anticancer agents such as merbarone or methotrexate can be incorporated.

The bioactive agents can be incorporated by dissolution or dispersion into the coating solution prior to coating, or by imbibing into coated layers. Dispersion of silver salts can be made by forming the salt in situ from soluble starting components or by dispersing insoluble components using methods known to those skilled in the art. Many of the organic agents can be dissolved directly into the coating liquid. Agents such as merbarone, free base forms of norfloxacin and gentamicin are directly soluble in the solvents of the invention. Other agents that are typically ionic and that are usually available in salt forms usually must be converted into organic salts in order to be soluble in the solvents of the invention. For instance, gentamicin sulfate can be converted into the lauryl sulfate salt which is readily soluble in the solvents of the invention. Sodium heparin is usually converted into a salt of a quaternary ammonium compound such as benzalkonium chloride which is readily soluble in the solvents of the invention. Sodium methotrexate can be converted into a salt of a quaternary compound such as benzalkonium chloride which is readily soluble with solvents of the invention. Other combinations that are suitable to accomplish the invention will occur to those skilled in the art.

The method of the invention is beneficial because the components can be varied to control lubricity, stability, swelling, flexibility, adhesion, and resistance to removal by wet abrasion. These characteristics of the coating can thus be adjusted for various substrates and applications. The method is also beneficial because the solutions of the invention have good shelf stability and remain substantially free of precipitate for periods in the range of months or years, so that various mixtures of the solutions for coatings may be prepared at one time and used to coat substrates later. Alternatively, the hydrophilic and hydrophobic stabilizing polymers, and other components may even be prepared in a single solution.

Substantially all of the polymers deposited from solutions onto the surface of the object being coated remain in the layer of the coating after the solvents are evaporated. The duration and temperature of the evaporating step may be selected to achieve stability of the coating layer and to achieve a bond between the surface being coated and the coating layer.

Preferably, in a multi-layer or multiply embodiment, the outer layer solution contains some amount of an "active" solvent, i.e., a cosolvent, for the outer layer ingredients as well as the inner layer ingredients. As such, the active solvent causes the outer layer solution to penetrate into the inner layer, and is believed to bring about a mixing at the molecular level of the components of both layers.

It is believed that such molecular mixing may only comprise physical mixing without chemical reaction(s). In any event, in a preferred embodiment, there is a high degree of intermolecular mingling between the hydrophilic polymer and the stabilizing polymer in the coating, and in particular in a multi-layer coating, at the interface between the inner and outer layers of the coating relative to the outer surface of the outer layer. In practice, the activity of the solvent mixture is adjusted so that the degree of penetration of the outer layer into the inner layer is in a useful range. For example, if the outer layer solvent mixture is too active toward the inner layer, then too much penetration into the inner layer occurs, and the outer layer will not be sufficiently lubricious when wet. Conversely, if the outer layer solvent is too inactive toward the inner layer, then too little penetration of outer layer into the inner layer occurs, and the coating is too easily removed from the inner layer by wet abrasion.

In an embodiment of the present invention, the lubricious hydrophilic layer and/or stabilizing polymer and/or bioactive agent is applied directly onto a polymer surface, and an active solvent is used which is a cosolvent for both the plastic substrate polymer or polymer mixture or at least one or more of the polymers in cases of mixed polymer substrates, and for the coating polymer(s) in the coating layer. After drying, the top coat polymer(s) layer is left partially embedded in the polymer surface. As in the case of the two-layer system, the solvent used during the coating application can be too active such that the top coat penetrates into the polymer surface to such a degree that the coated layer behaves as though it has been highly cross-linked. This prevents the top coat from becoming sufficiently swollen and lubricious when wet by aqueous fluids. In the case of a bioactive agent, it may not be exposed sufficiently to provide a physiological effect. Solvent mixtures can also be too inactive so that the coating is not resistant enough to abrasion when wet and is too easily removed.

The active solvents which are useful in the present invention may be individual solvents or solvent mixtures containing two or more solvents. In the case of solvent mixtures, one or more of the solvents in the mixture may be active while other solvent(s) in the mixture may be inactive. In any event, the solvent or solvent mixture dissolves or at least disperses the hydrophilic coating polymer and/or bioactive agent. In cases where the active agent is dispersed but not dissolved, a point is reached where the active agent goes into solution before all of the solvent has left the coating. During the phase of drying where the active agent is in solution, the solvent has also penetrated the substrate polymer(s) of the polymer surface. Thus, intermolecular mingling may take place between the substrate polymer(s) and the hydrogel polymer(s).

Examples of active solvents useful in the present invention include butyrolactone, alcohols, dimethyl acetamide, and n-methyl-2-pyrrolidone. These solvents and others cause different degrees of swelling of the plastic substrate or inner layer, as the case may be.

When tested by subjective methods the hydrogel coatings of the invention, when wet, are more slippery than wet, greased glass, and, when dry, are no more slippery than dry glass. The coatings of the invention are resistant to removal by wet abrasion as determined by running water over the coatings and rubbing between tightly gripped fingers while wet. The inventive coatings have high adherence when dry, as determined by attaching adhesive tape, pulling the tape off with a vigorous action, and then wetting the coated substrate to determine whether the taped portion retained the lubricant coating. The inventive coatings remain adherent and coherent for extended periods when stored in water, and neither peel off, dissolve, nor dissociate.

Suitable combinations of substrates, polymers, and solvents will be apparent to skilled practitioners. Generally, increasing the ratio of stabilizing polymer to water soluble polymer increases wet rub resistance and reduces lubricity. At high ratios, the hydrogel is not lubricious, and the coating can even be made to be hydrophobic. At low ratios, the hydrogel swells more in water and is less resistant to wet rub-off. The hydrogel may become impermanent or wash off easily.

The interaction between the stabilizing polymer and the hydrophilic polymer and/or the bioactive agent may be controlled to promote molecular entanglement. For example, the choice of solvent plays an important role. If a solvent is selected that allows a hydrogel layer to penetrate into the substrate layer, molecular entanglement at the interface layer results. This leads to increased wet rub resistance and decreased lubricity. Such factors may be taken into account by those skilled in the art when practicing this invention.

Examples of substrates and stabilizing polymer formulations that are effective with them are listed below. Many other combinations will be apparent to a person of ordinary skill following the teachings of the invention.

| | |
|---|---|
| polyurethane: | hydroxyl function acrylic polymer; acrylic dispersion polymer; styrene acrylic copolymer; epoxy plus polyamide |
| polyethylene: | carboxyl function and hydroxyl function acrylic polymers plus melamine plus epoxy |
| silicone: | carboxyl function acrylic polymer plus epoxy resin |
| polyvinyl-chloride: | hydroxyl function acrylic polymer; polyvinylbutyral plus phenolic resin |
| acetal: | ethylene vinyl acetate copolymer; polyvinyl acetate copolymer |
| glass: | ethylene acrylic acid copolymer plus melamine resin plus acrylic polymer plus hydroxyl function acrylic polymer |
| stainless steel | epoxy plus polyamide, ethylene acrylic acid copolymer; acrylic polymer with carboxyl function plus epoxy resin. |

The following examples show how the invention can be used. All amounts are given in grams except as indicated.

EXAMPLE 1

Polyurethane tubing was dip coated in the following solution, and dried 45 minutes at 85° C.

| | |
|---|---|
| PVP | 0.289 |
| Benzyl alcohol | 1.563 |
| Ethanol | 2.801 |
| Cyclohexanone | 5.347 |
| Acrylic polymer with hydroxyl function | 0.050 |
| Xylene | 0.050 |

Results

The coating was tested for adhesion by cutting lines through it with a knife and then rubbing briskly across the cuts with a finger after the coating was immersed in water. No failure of adhesion (i.e., peel back) occurred after the wet rub test. Next, the coating dry adhesion was tested by pressing Universal Tape 83436 tape (United Stationers Supply, Co.) firmly onto the coating and peeling the tape off briskly. No coating should be removed by this test. This sample showed no adhesion failure on the tape test. This coating had good lubricity when wet.

EXAMPLE 2

Oxygen plasma treated polyethylene tubing was dip coated in the following solution, and dried 45 minutes at 85° C.

| | |
|---|---|
| 5% (w/w) ethylene acrylic acid copolymer in THF | 15.0 |
| Cyclohexanone | 4.0 |
| Hydroxyl function acrylic polymer | 0.24 |
| Melamine resin | 0.06 |
| 80% (w/w) isocyanate polymer in THF | 0.32 |
| Trichloroacetic acid | 0.20 |

After the oven drying process, the sample was dip coated in the following solution and dried 1 hour at 80° C.

| | |
|---|---|
| THF | 74.00 |
| Xylene | 0.25 |
| Acrylic copolymer with carboxyl function | 13.88 |
| Epoxy resin | 0.75 |
| Aromatic 150 solvent | 9.73 |
| Butyl Cellosolve | 1.39 |

Next, the sample was dip coated in the following hydrogel solution and dried 1 hour at 80° C.

| | |
|---|---|
| Butyrolactone | 1.80 |
| Dimethylacetamide | 1.20 |
| Ethanol | 8.75 |
| PVP | 0.25 |
| THF | 0.60 |
| Xylene | 0.05 |
| Epoxy resin | 0.10 |
| Polyamide resin | 0.05 |

Results

This coating showed good dry adhesion, good lubricity, and good wet rub resistance when tested as per Example 1.

EXAMPLE 3 (COMPARATIVE)

This example compares improved coatings of the invention to the PVP-cellulose ester coatings of U.S. PAT. No. 5,331,027, and shows that the inventive coatings yield superior adhesion. Samples of silicone tubing were treated with an oxygen plasma process. Next, they were dip coated in the following solution and dried 120 minutes at 80° C.

| | |
|---|---|
| Acrylic copolymer with carboxyl function | 5.0 |
| Aromatic 150 solvent | 3.5 |
| Butyl cellosolve | 0.5 |
| THF | 27.75 |
| Epoxy resin | 0.56 |
| Xylene | 0.19 |

Next, Sample A was dip coated with the same hydrogel solution that was used in Example 2. Sample B was dip coated in the following solution for comparison (an example of the PVP-cellulose ester preparation of U.S. Pat. No. 5,331,027) and dried 2 hours at 80° C.

| | |
|---|---|
| PVP | 31.74 |
| Ethanol | 462.01 |
| Butyrolactone | 103.75 |
| Cyclohexanone | 12.82 |
| Nitrocellulose | 0.008 |

Results

The two coated samples were tested as per Example 1. The Sample A coated with the same hydrogel as Example 2 showed good wet and dry adhesion and wet peel resistance, and was lubricious. Under the same test conditions Sample B coated with the PVP-cellulose ester hydrogel solution failed the dry adhesion and wet peel tests, showing that the coatings of this invention are superior to the prior technology.

EXAMPLE 4

The following solution was dip coated on polyurethane tubing and dried for 45 minutes at 85° C.

| | |
|---|---|
| Ethanol | 1.88 |
| Benzyl alcohol | 3.36 |
| Cyclohexanone | 6.42 |
| PVP | 0.35 |
| Xylene | 0.10 |
| Acrylic copolymer with hydroxyl function | 0.10 |

Results

This sample had good wet lubricity, wet adhesion, wet rub resistance, and dry adhesion when tested as per Example 1.

EXAMPLE 5

The following solution was dip coated on polyurethane tubing and dried for 45 minutes at 85° C.

| | |
|---|---|
| Ethanol | 1.88 |
| Benzyl alcohol | 3.36 |
| Cyclohexanone | 6.42 |
| PVP | 0.35 |
| Crosslinkable acrylic aqueous emulsion (46% solids) | 0.20 |

Results

This sample had good wet and dry adhesion, good peel resistance, and was lubricious when tested as per Example 1.

EXAMPLE 6

A sample of PVC tubing was dip coated in the following solution and dried 45 minutes at 85° C.

| | |
|---|---|
| Ethanol | 1.88 |
| Benzyl alcohol | 3.36 |
| Cyclohexanone | 6.42 |
| PVP | 0.35 |
| Xylene | 0.10 |
| Acrylic polymer with hydroxyl function | 0.10 |

Results

This sample had good wet lubricity, wet adhesion, wet rub resistance, and dry adhesion when tested as per Example 1.

EXAMPLE 7

PVC tubing was dip coated in the following solution and dried for 30 minutes at 85° C.

| | |
|---|---|
| Ethanol | 1.88 |
| Benzyl alcohol | 3.36 |

-continued

| | |
|---|---|
| Cyclohexanone | 6.42 |
| PVP | 0.49 |
| Xylene | 0.15 |
| Acrylic polymer with hydroxyl function | 0.15 |

Results

This sample had good wet and dry adhesion and wet peel/rub resistance to removal and was lubricious when tested as per Example 1.

EXAMPLE 8 (COMPARATIVE)

This example compares the coatings of this invention to the PVP-cellulose ester coatings of U.S. PAT. No. 5,331,027 and shows that the inventive coatings yield superior adhesion. Samples of Nitinol wire (nickel-titanium alloy) coated with an aliphatic polyurethane were coated with one or the other of the following solutions, and dried for 1 hour at 85° C.

| Sample A. Inventive technology | |
|---|---|
| Ethanol | 1.88 |
| Benzyl alcohol | 3.36 |
| Cyclohexanone | 6.42 |
| PVP | 0.49 |
| Xylene | 0.15 |
| Acrylic polymer with hydroxyl function | 0.15 |
| Sample B. Prior art (i.e., 5,331,027) | |
| Ethanol | 1.88 |
| Benzyl alcohol | 3.36 |
| Cyclohexanone | 6.42 |
| PVP | 0.35 |
| Nitrocellulose solution 0.0625% in cyclohexanone | 0.14 |

Results

Sample A according to the invention had good wet and dry adhesion, good lubricity and good wet rub resistance. Sample B had poor wet adhesion, and poor wet rub resistance (the entire coating wiped off easily when wet). This comparison demonstrated the superiority of this invention over the prior art.

EXAMPLE 9

The following solution was dip coated on an acetal surface, air dried for 10 minutes and oven dried for 30–60 minutes at 85° C.

| | |
|---|---|
| Ethylene vinyl acetate copolymer | 1.5 |
| THF | 10.8 |
| Cyclohexanone | 2.7 |

Next, the sample was coated with the following hydrogel solution and was air dried for 10 minutes and oven dried for 30–60 minutes at 85° C.

| | |
|---|---|
| PVP | 0.75 |
| Ethanol | 11.40 |
| Benzyl alcohol | 2.85 |

Results

This sample was lubricious and resistant to wet rub off and had good wet and dry adhesion.

EXAMPLE 10

Example 9 was repeated except that the coating that was applied under the hydrogel consisted of the following:

| | | |
|---|---|---|
| Polyvinyl acetate | 4.0 | |
| Ethanol | 12.8 | |
| Benzyl alcohol | 3.2 | |

Results

This sample was lubricious and resistant to wet rub off, and had good wet and dry adhesion.

EXAMPLE 11

The following was brush coated on a glass slide and dried 30 minutes at 85° C.

| | | | |
|---|---|---|---|
| Precoat- | 5% (w/w) ethylene acrylic acid copolymer in THF | 15.0 | |
| | Cyclohexanone | 4.0 | |
| | Hydroxyl function acrylic polymer | 0.24 | |
| | Melamine resin | 0.06 | |
| | 80% (w/w) isocyanate | 0.32 | |
| | Trichloroacetic acid | 0.20 | |

Next, the following coating was applied and dried for 60 minutes at 85° C.

| | | | |
|---|---|---|---|
| Basecoat- | 30% (w/w) acrylic polymer in toluene | 9.9 | |
| | Cyclohexanone | 8.8 | |
| | Benzyl alcohol | 4.8 | |
| | Polyurethane | 0.86 | |
| | THF | 7.74 | |
| | Hydroxyl function acrylic polymer | 1.80 | |
| | Melamine resin | 0.45 | |
| | Trichloroacetic acid | 0.1 | |
| | Xylene | 1.76 | |
| | Butanol | 0.49 | |

Next, the hydrogel of Example 9 was applied and oven dried at 85° C for 30–60 minutes.

Results

This sample had good adhesion and lubricity.

EXAMPLE 12

The following was coated on a polyurethane tube and dried 60 minutes at 85° C.

| | |
|---|---|
| Ethanol | 18.8 |
| Benzyl alcohol | 33.6 |
| Cyclohexanone | 64.2 |
| PVP | 3.5 |
| Acrylic polymer with carboxyl function | 1.11 |
| Aromatic 150 solvent | 0.78 |
| Butyl cellosolve | 0.11 |
| THF | 1.67 |
| Epoxy resin | 0.25 |
| Xylene | 0.08 |

Results

This sample was lubricious and resistant to wet abrasion and had good adhesion.

EXAMPLE 13

The following solution was coated on polyurethane tubing and dried for 18 hours at 85° C.

| | |
|---|---|
| Ethanol | 1.8 |
| Benzyl alcohol | 3.36 |
| Cyclohexanone | 6.42 |
| PVP | 0.35 |
| Styrene acrylic copolymer | 0.20 |
| Water | 0.20 |

Results

This sample was lubricious and resistant to wet abrasion and had good adhesion.

EXAMPLE 14

A stainless steel wire was coated with the following precoat and was dried for 60 minutes at 85° C.

| | |
|---|---|
| 5% (w/w) ethylene acrylic acid copolymer in THF | 15.0 |
| Epoxy resin | 0.17 |
| Xylene | 0.06 |
| THF | 0.23 |

Next, the sample was coated with the following solution and dried 1 hour at 85° C.

| | |
|---|---|
| Epoxy resin | 0.37 |
| Polyamide resin | 0.18 |
| Xylene | 0.20 |
| THF | 6.24 |
| PVP-vinylacetate copolymer | 0.25 |
| Ethanol | 0.25 |
| Cyclohexanone | 1.00 |
| Tridodecylmethyl ammonium heparinate | 0.10 |

This sample was not designed to be lubricious. It had good wet and dry adhesion.

EXAMPLE 15

The following solution was dip coated on polyurethane tubing and dried 60 minutes at 85° C.

| | |
|---|---|
| Ethanol | 1.88 |
| Benzyl alcohol | 3.36 |
| Dimethylacetamide | 4.00 |
| Cyclohexanone | 6.42 |
| PVP | 0.35 |
| Merbarone (a non-ionic cancer agent) | 0.07 |
| Acrylic copolymer with hydroxyl function | 0.15 |
| Xylene | 0.15 |

Results

This sample of a medicated coating had good wet and dry adhesion and was resistant to wet abrasion.

EXAMPLE 16

The following solutions were coated on 5 Fr. polyurethane tubing and dried for 20 minutes at 85° C.

| Solution 16A | |
| --- | --- |
| Toluene | 4.00 |
| Xylene | 0.15 |
| IPA | 3.00 |
| Hydroxyl function acrylic copolymer | 0.15 |
| Cyclohexanone | 1.00 |
| 50% (w/w) solution of PVP/VA in ethanol | 0.50 |
| Benzalkonium heparinate | 0.10 |
| Solution 16B | |
| Toluene | 7.00 |
| IPA | 2.00 |
| Cyclohexanone | 2.00 |
| 50% (w/w) solution of PVP/VA in ethanol | 0.50 |
| Acrylic polymer with hydroxyl function | 0.20 |
| Xylene | 0.20 |
| Solution 16C | |
| Gensolve 2004 | 7.0 |
| Cyclohexanone | 1.0 |
| Tridoclecdlmethyl ammonium heparinate | 0.20 |
| 50% (w/w) ethanolic solution of PVP/VA | 0.50 |
| Hydroxyl function acrylic copolymer | 0.20 |
| Xylene | 0.20 |

Solutions 16A, 16B, and 16C were dip coated on polyurethane tubing and dried for 20 minutes at 85° C. Next, the samples were tested for anti-clotting activity according to the appended clotting assay.

Results

Plasma clotted in minutes when exposed to the uncoated polyurethane tubing. The plasma did not clot even after exposure overnight to any of the three coated samples of Example 16. This demonstrates the strong antithrombogenic activity of the coatings.

EXAMPLE 17

A stainless steel wire (0.025" diameter) was dip coated with the following solution, and dried 60 minutes at 85° C.

| 5% (w/w) polyethylene acrylic acid copolymer in THF | 10.0 |
| --- | --- |
| Epoxy resin | 0.113 |
| Xylene | 0.038 |
| THF | 0.15 |
| Cyclohexanone | 2.0 |

Next, the wire was dip coated in the same heparin containing hydroxyl coating solution as in Example 16A, and dried 20 minutes at 85° C. Next, the coated samples were tested for anticlotting activity using the same methods that were used in Example 16.

Results

The plasma clotted in minutes when exposed to the uncoated stainless steel. The plasma that was exposed to the coated sample did not clot overnight, demonstrating the strong antithrombogenic activity of the coating.

EXAMPLE 18

The following solution was prepared.

| Xylene | 0.60 |
| --- | --- |
| THF | 34.52 |
| Epoxy resin | 0.90 |
| Polyamide | 0.48 |
| DNA | 5.00 |
| PVP | 3.10 |
| Ethanol | 22.05 |

Next, various antimicrobial agents were mixed with 8.0 gm of the above solution.

| Gentamycin free base | 0.08 - dissolved |
| --- | --- |
| Norfloxaxin free base | 0.08 - dissolved |
| Rifamycin SV | 0.09 - dissolved |
| Silver Sulfadiazine | 0.08 - dispersed |

Each solution was coated in 5 Fr polyurethane tubing and dried 45 minutes at 85° C. Next, the coated samples were tested for antimicrobial activity by "zone of inhibition" testing vs E. epi. Two samples of each were tested.

| Results: | |
| --- | --- |
| Antimicrobial Agents | Zone of Inhibition (cm) |
| Gentamycin free base | 1.9/2.0 |
| Norfloxacin free base | 2.5/2.5 |
| Rifamycin SV | 4.5/4.5 |
| Silver Sulfadiazine | 0.7/0.7 |

These results demonstrate how various antimicrobial agents can be incorporated into the coatings of the invention while exhibiting their strong antimicrobial activity. It is expected that other types of agents can be incorporated into the coatings and be able to exert their activity in the region of the surface coating. For instance, agents could be incorporated in the coatings to treat cancer or restenoses in patients.

EXAMPLE 19

Polyurethane tubing was coated with the following solution and dried 20 minutes at 85° C.

| Gensolve 2004 | 7 |
| --- | --- |
| Cyclohexanone | 1 |
| 50% (w/w) ethanolic solution of PVP-vinylacetate copolymer | 0.5 |
| 50% solution of hydroxyl function acrylic polymer in xylene | 0.4 |
| Stearyldimethylbenzyl ammonium heparinate | 0.2 |

The sample was tested in the clotting assay of Example 16. The plasma did not clot even after exposure overnight.

EXAMPLE 20 (COMPARATIVE)

The following solution was prepared.

| Solution 20A | |
| --- | --- |
| RS Nitrocellulose | 25.2 |
| Toluene | 11.3 |
| Butyl acetate | 17.0 |
| Ethyl acetate | 34.8 |

-continued

| Solution 20A | |
|---|---|
| Dibutylphthalate | 6.6 |
| Camphor | 4.8 |
| 2-Hydroxy-4-Methyl-Benzophenone | 0.3 |

Next, the following solutions were made. 20B is representative of the technology of U.S. Pat. No. 5,001,009.

| Solution 20B | |
|---|---|
| Solution 20A | 31.9 |
| Cyclohexanone | 22.8 |
| Benzyl alcohol | 22.8 |
| Ethyl acetate | 17.8 |
| Iron Blue RS dispersion (Penn color) | 2.3 |
| Brown Oxide dispersion (Penn color) | 0.7 |
| TiO₂ dispersion (Penn color) | 1.6 |

| Solution 20C | |
|---|---|
| This is representative of the invention. | |
| THF | 67.5 |
| Polyurethane resin | 2.5 |
| Cyclohexanone | 10.0 |
| Polyvinylbutyral | 3.6 |
| Phenolic resin | 2.8 |

Next, solutions 20B and 20C were brush coated on an untreated flat inert polyethylene surface and dried for 60 minutes at 85° C. The colorants are known not to affect flexibility or adhesion. The polyurethane is an optional ingredient in this type of coating that is not necessary to confer flexibility. After cooling to room temperature, the coatings were peeled off the inert plastic surface to evaluate flexibility without the muting effect of the substrate. Such a coating will adhere to most substrates adequately although plasma treatment as in Example 2 or a pre-coat may be appropriate for larger flat applications.

Results

The 20B sample (prior art technology) cracked and broke into small brittle pieces. The 20C sample (inventive technology) peeled off evenly and was very flexible. It could be bent over tightly on itself and did not crack or fracture. It remained as a continuous, rubbery film that could be stretched without breaking. Flexibility of the peeled coating without cracking is predictive of coherence and flexibility as applied to a substrate. Flexibility as opposed to cracking of a peeled coating is predictive of a decreased likelihood of coating failure especially on substrates of smaller diameter and those expected to be subjected to extensive flexing. This demonstrates superior flexibility of the instant invention technology over conventional coatings.

EXAMPLE 21 (COMPARATIVE)

The following solutions were made.

| Solution 21A | |
|---|---|
| Solution 20A | 37.7 |
| Cyclohexanone | 19.5 |
| Benzyl alcohol | 10.6 |
| 10% (w/w) polyurethane resin solution in THF | 19.0 |
| 50% (w/w) hydroxyl function acrylic polymer solution in Xylene/Butanol (78/22) | 10.00 |
| Trichloroacetic acid | 0.1 |
| 7.5% (w/w) Iron Blue dispersion (Penn color) | 1.0 |
| 32.0% (w/w) TiO₂ dispersion (Penn color) | 1.4 |
| 11% (w/w) Brown Oxide dispersion Penn color) | 0.7 |

| Solution 21B | |
|---|---|
| THF | 74.0 |
| Xylene | 0.25 |
| Acrylic polymer with carboxyl function | 13.88 |
| Epoxy resin | 0.75 |
| Aromatic 150 solvent | 9.73 |
| Butyl cellosolve | 1.39 |

The solutions were dip coated on separate samples of 0.020 inch stainless steel coil guide wires which dried for 60 minutes at 85° C. Both coated guidewire samples were tested by pulling them tightly around a ¼" mandril and inspecting them for cracks in the coatings.

Results

The wire sample coated with 21A solution (prior art technology) had cracks, and sections between the cracks were straight. The sample coated with the technology of this invention had no cracks, and had a smooth, continuous arc as it bent around the mandril. This demonstrates the greater flexibility of this technology, and shows how it improves the flexibility of substrates coated with it compared to the prior art, especially on thinner (i.e. <0.050" diameter) devices that are designed to be flexible and which must be capable of maneuvering around multiple, relatively tight bends during use.

EXAMPLE 22

The following solution was dip coated on PVC tubing and air dried for 60 seconds.

| Solution 22A | |
|---|---|
| Polyurethane resin | 3.0 |
| Methylethylketone | 42.9 |
| N-methyl-2-pyrrolidone | 15.0 |
| THF | 32.6 |
| Phenolic resin | 5.1 |
| Polyvinylbutyral resin | 0.3 |
| Butanol | 1.1 |

Next, the sample was dip coated in the following solution and dried at 80° C for 1–2 hours.

| | |
|---|---|
| PVP | 4.0 |
| Ethanol | 34.5 |
| Benzyl alcohol | 30.0 |
| Isopropanol | 30.0 |
| Polyethylieneglycol 400 | 1.5 |

This sample had good wet lubricity and good adhesion.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. A coating applied to a surface of a medical device, the coating comprising:
   (a) a stabilizing polymer selected from the group consisting of polymers based on cross-linkable acrylic and methacrylic polymers crosslinked with a crosslinker, ethylene acrylic acid copolymers, styrene acrylic copolymers, polyvinyl acetals, ethylene vinyl acetate copolymer, polyvinyl acetate, epoxy resins, amino resins, phenolic resins, copolymers thereof, and combinations; and
   (b) an active agent selected from the group consisting of a hydrophilic polymer selected to interact with the stabilizing polymer so as to produce a lubricious hydrogel, a bioactive agent, and a combination,
   the active agent being entrapped in the stabilizing polymer such that the coating adheres to the surface when dry and when wet, and remains coherent without cracking upon flexing of the surface.

2. A coating according to claim 1, wherein the stabilizing polymer is cross-linkable and further comprising a cross-linker for the stabilizing polymer.

3. A coating according to claim 2, wherein the cross-linker is selected from the group consisting of epoxy resin, melamine resin, other amino resin, and phenolic resin.

4. A coating according to claim 1, in which the stabilizing polymer has at least one component selected from the group consisting of acrylic with carboxyl, hydroxyl, amide, and methylol functional groups.

5. A coating according to claim 1, in which the surface of the medical device comprises a material selected from the group consisting of stainless steel, nickel, gold, chrome, nickel titanium alloy, platinum, another metal, silicone, polyethylene, other polyolefins, polyamide, polyesters, other plastics, glass, polyurethane, acetal, and polyvinyl chloride.

6. A coating according to claim 1, wherein the medical device is selected from the group consisting of needles, guide wires, catheters, surgical instruments, equipment for endoscopy, wires, stents, angioplasty balloons, wound drains, wound dressings, arteriovenous shunts, gastroenteric tubes, urethral inserts, laparoscopic equipment, pellets, and implants.

7. A coating according to claim 1, in which the stabilizing polymer is a cross-linkable acrylic selected from the group consisting of methylmethacrylate, butylmethacrylate, isobutylmethacrylate, ethylmethacrylate, methylacrylate, ethylacrylate, acrylic acid, methacrylic acid, styrene methacrylate, and styrene acrylate, and copolymers thereof.

8. The coating of claim 1 wherein the bioactive agent is selected from the group consisting of a pharmaceutical agent, a salt, an osmotic agent, and an oligonucleotide.

9. The coating of claim 1 further comprising an additive selected from the group consisting of a surfactant, a colorant, and a plasticizer.

10. The coating according to claim 1, wherein the coating comprises inner and outer layers having different proportions of the stabilizing polymer and the active agent.

11. The coating according to claim 1, wherein the coating thickness is less than about 50 microns.

12. The coating according to claim 1, wherein the active agent is a hydrophilic polymer and the coating is a hydrogel.

13. The coating according to claim 1, wherein the active agent is a bioactive agent.

14. The coating according to claim 12, wherein the coating comprises a bioactive agent.

15. The coating according to claim 1, wherein the coating resists wet abrasion and remains coherent despite flexing when applied to stainless steel.

16. The coating according to claim 1, wherein the selection of stabilizing polymer is independent of whether the stabilizing polymer is present in the substrate.

17. A method for coating a medical device having an inert surface comprising:
   applying to the surface a coating liquid comprising a stabilizing polymer selected from the group consisting of polymers based on cross-linkable acrylic and methacrylic polymers, ethylene acrylic acid copolymers, styrene acrylic copolymers, polyvinyl acetals, ethylene vinyl acetate copolymer, polyvinyl acetate, epoxy resins, amino resins, phenolic resins, copolymers thereof, and combinations; and
   applying a coating liquid comprising an active agent selected from the group consisting of a hydrophilic polymer selected to interact with the stabilizing polymer so as to produce a lubricious hydrogel, and a bioactive agent, and a combination, and
   drying to remove liquids such that the crosslinkable acrylic and methacrylic polymers become crosslinked, the active agent is entrapped by the stabilizing polymer and the coating adheres to the surface when dry and wet, and remains coherent despite flexing of the surface.

18. A method according to claim 17, in which a single coating liquid comprises both the stabilizing polymer and the active agent.

19. A method according to claim 17, in which the applying step comprises dipping, spraying, brushing, or wiping.

20. A method according to claim 17, further comprising pretreating the surface of the medical device by gas plasma or other ionizing treatment before the applying step.

21. A method according to claim 17, wherein the drying comprises heating the coating to at least about 50° C.

22. A method for coating a medical device comprising a surface polymer selected from the group consisting of polymers based on cross-linkable acrylics, amino resins, phenolic resins, epoxy resins, polyvinylacetals, ethylene vinyl acetate copolymer, polyvinylacetate, copolymers thereof, and combinations; the method comprising the steps of
   (a) applying a coating liquid comprising a solvent capable of attacking the device surface, and an active agent selected from the group consisting of a hydrophilic polymer selected to interact with the surface polymer so as to produce a lubricious hydrogel, and a bioactive agent, and a combination, and
   (b) drying the coating liquid such that the crosslinkable acrylics become crosslinked, the active agent is entrapped in the surface polymer and the coating adheres to the surface when dry and wet, and remains coherent despite flexing of the medical device.

23. A kit for applying a coating to a medical device, comprising:
   a liquid comprising a stabilizing polymer selected from the group consisting of polymers based on cross-linkable acrylic and methacrylic polymers crosslinked with a crosslinker, ethylene acrylic acid copolymers, styrene acrylic copolymers, polyvinylacetals, ethylene vinyl acetate copolymer, polyvinylacetate, epoxy resins, amino resins, phenolic resins, copolymers thereof, and combinations; and a liquid comprising an active agent selected from the group consisting of a hydrophilic polymer selected to interact with the stabilizing polymer so as to produce a lubricious hydrogel, and a bioactive agent, and a combination, the liquids being the same or separate, and the stabilizing polymer and the active agent being selected to produce on the medical device a coherent flexible coating that has wet and dry adhesion.

24. The kit of claim 23, wherein the liquids are separate.

25. The kit of claim 24, wherein the liquid comprising the active agent further comprises a stabilizing polymer.

26. The kit of claim 24, wherein the liquid comprising the stabilizing polymer further comprises an active agent.

27. The kit of claim 23, wherein the liquid or liquids comprise a solvent selected from the group consisting of water, xylene, tetrahydrofuran, cyclohexanone, ethanol, butyrolactone, butanol, trichloroacetic acid, benzyl alcohol, isobutyl acetate, methyl ethyl ketone, Aromatic 150, toluene, and butyl cellosolve.

28. The kit of claim 23, wherein the stabilizing polymer liquid is an aqueous cross linkable acrylic dispersion.

29. The kit of claim 23, comprising a liquid comprising a cross-linker for the stabilizing polymer.

30. A medical device comprising a coating according to claim 1.

31. A coating according to claim 1 wherein the stabilizing polymer is selected from the group consisting of cross-linkable acrylic and methacrylic polymers, ethylene acrylic acid copolymers, styrene acrylic copolymers, vinyl acetate polymers, vinyl acetate copolymers, vinyl acetal polymers, vinyl acetal copolymers, epoxy, melamine, other amino resins, phenolic polymers, copolymers thereof, and combinations.

32. The coating according to claim 1, consisting essentially of the stabilizing polymer and the active agent.

33. A medical device comprising a coating according to claim 1 having a combination of substrate coated with stabilizing polymer formulation selected from the group consisting of: (a) polyurethane coated with stabilizing polymer formulation selected from the group consisting of one or more of styrene acrylic copolymer, and epoxy plus polyamide; (b) polyethylene coated with stabilizing polymer formulation selected from the group consisting of one or more of carboxyl function and hydroxyl function acrylic polymers plus melamine plus epoxy; (c) silicone with carboxyl function acrylic polymer plus epoxy resin; (d) polyvinylchloride coated with polyvinylbutyral plus phenolic resin; (e) acetal coated with stabilizing polymer formulation selected from the group consisting of one or more of ethylene vinyl acetate copolymer and polyvinyl acetate copolymer; (f) glass coated with ethylene acrylic acid copolymer plus melamine resin plus acrylic polymer plus hydroxyl function acrylic polymer; and (g) stainless steel coated with stabilizing polymer formulation selected from the group consisting of one or more of epoxy plus polyamide/ethylene acrylic acid copolymer, and acrylic polymer with carboxyl function plus epoxy resin.

34. A coated medical device produced by the method of claim 17.

35. A coated medical device produced by applying a kit according to claim 23 to a surface of the device.

36. A coating applied to a surface of a medical device, the coating comprising:

(a) a stabilizing polymer selected from the group consisting of polymers based on cross-linkable acrylic and methacrylic polymers, ethylene acrylic acid copolymers, styrene acrylic copolymers, polyvinyl acetals, ethylene vinyl acetate copolymer, polyvinyl acetate, epoxy resins, amino resins, phenolic resins, copolymers thereof, and combinations; and (b) an active agent selected from the group consisting of a hydrophilic polymer selected to interact with the stabilizing polymer so as to produce a lubricious hydrogel, a bioactive agent, and a combination, the active agent being entrapped in the stabilizing polymer such that the coating adheres to the surface when dry and when wet, and remains coherent without cracking upon flexing of the surface.

37. A coating according to claim 36, in which the stabilizing polymer has at least one component selected from the group consisting of acrylic with carboxyl, hydroxyl, amide, or methylol functional groups.

38. A coating according to claim 36, in which the surface of the medical device comprises a material selected from the group consisting of stainless steel, nickel, gold, chrome, nickel titanium alloy, platinum, another metal, silicone, polyethylene, other polyolefins, polyamide, polyesters, other plastics, glass, polyurethane, acetal, and polyvinyl chloride.

39. A coating according to claim 36, wherein the medical device is selected from the group consisting of needles, guide wires, catheters, surgical instruments, equipment for endoscopy, wires, stents, angioplasty balloons, wound drains, wound dressings, arteriovenous shunts, gastroenteric tubes, urethral inserts, laparoscopic equipment, pellets, and implants.

40. A medical device comprising a coating according to claim 36 having a combination of substrate coated with stabilizing polymer formulation selected from the group consisting of: (a) polyurethane coated with stabilizing polymer formulation selected from the group consisting of one or more of hydroxyl function acrylic polymer, crosslinkable acrylic dispersion polymer, styrene acrylic copolymer, and epoxy plus polyamide; (b) polyethylene coated with stabilizing polymer formulation selected from the group consisting of one or more of carboxyl function and hydroxyl function acrylic polymers plus melamine plus epoxy; and (c) polyvinylchloride coated with stabilizing polymer selected from the group consisting of hydroxy function acrylic polymer and polyvinylbutyral plus phenolic resin.

* * * * *